US00PP35966P2

(12) United States Plant Patent
Wilde

(10) Patent No.: US PP35,966 P2
(45) Date of Patent: Jul. 2, 2024

(54) ***SUTERA* PLANT NAMED 'KLESG22036'**

(50) Latin Name: *Sutera grandiflora*
Varietal Denomination: KLESG22036

(71) Applicant: KLEMM + SOHN GMBH & CO. KG, Stuttgart (DE)

(72) Inventor: Katinka Wilde, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/213,611

(22) Filed: Jun. 23, 2023

(51) Int. Cl.
*A01H 5/02* (2018.01)
*A01H 6/00* (2018.01)

(52) U.S. Cl.
USPC ..... Plt./485

(58) Field of Classification Search
USPC ..... Plt./485
CPC ..... A01H 5/02; A01H 5/00; A01H 6/00
See application file for complete search history.

(56) References Cited

U.S. PATENT DOCUMENTS

PP32,660 P3 * 12/2020 Winslow ..... A01H 6/00
Plt./485

* cited by examiner

*Primary Examiner* — June Hwu
(74) *Attorney, Agent, or Firm* — Weatherly IP Solutions, LLC; James M. Weatherly

(57) ABSTRACT

A new *Sutera* plant particularly distinguished by having large white flowers and short internode length, is disclosed.

1 Drawing Sheet

Genus and species: *Sutera grandiflora*.
Variety denomination: 'KLESG22036'.

BACKGROUND OF THE NEW PLANT

The present invention comprises a new and distinct variety of *Sutera*, botanically known as *Sutera grandiflora*, and hereinafter referred to by the variety name 'KLESG22036'. 'KLESG22036' originated from a controlled cross-pollination between the commercial female *Sutera* Scopia® Compact White (patent status unknown) and the proprietary male *Sutera* variety 'SG-2016-0688' (unpatented).

From May 2015 through July of 2015, controlled crosses between the female *Sutera* variety, Scopia® Compact White and the proprietary male *Sutera* variety 'SG-2016-0688' were undertaken in a foil house in Stuttgart, Germany. Seed was collected and cleaned in winter 2017. In January 2018, seed were sown and plants were grown for evaluation in Stuttgart, Germany in a greenhouse under glass. A plant line was selected in May 2018, which had a white flower color and subsequently named 'KLESG22036'. In May 2018, 'KLESG22036' was first vegetatively propagated by asexual cuttings in Stuttgart, Germany. 'KLESG22036' was found to reproduce true to type in successive generations of asexual propagation via asexual cuttings.

SUMMARY

The following are the most outstanding and distinguishing characteristics of this new variety when grown under normal horticultural practices in Stuttgart, Germany.

1. Large white flowers; and
2. Short internode length.

DESCRIPTION OF THE PHOTOGRAPH

This new *Sutera* plant is illustrated by the accompanying photograph which shows a close-up of the flowers. The photograph is of a 13-week-old plant grown in an indoor environment in Stuttgart, Germany in May 2021. The colors shown are as true as can be reasonably obtained by conventional photographic procedures.

DESCRIPTION OF THE NEW VARIETY

The following detailed descriptions set forth the distinctive characteristics of 'KLESG22036'. The data which define these characteristics were collected from asexual reproductions carried out in Stuttgart, Germany. Data was collected on 8-week-old plants from potting grown in a foil house where plant regulators were used three times in Stuttgart, Germany in April 2023. Color references are to The R.H.S. Mini Colour Chart of The Royal Horticultural Society of London (R.H.S.), (2005) in association with the Flower Council of Holland.

Classification:
- *Family*.—Scrophulariaceae.
- *Botanical*.—*Sutera grandiflora*.
- *Common*.—*Sutera*.
- *Designation*.—'KLESG22036'.

Parentage:
- *Female parent*.—*Sutera* Scopia® Compact White (patent status unknown).
- *Male parent*.—Proprietary *Sutera* line 'SG-2016-0688' (unpatented).

Plant:
- *Habit*.—Trailing and flat.
- *Height*.—6.0 cm.
- *Spread*.—23.5 cm.
- *Life cycle*.—Blooms from spring until September.
- *Form*.—Trailing and round.
- *Time to produce a rooted cutting*.—3 weeks.
- *Time to bloom from propagation*.—Finished product could be observed after 5-6 weeks after potting.

*Lastingness of inflorescence on the plant.*—About 7 days.
*Rooting habit.*—Fine, fibrous roots.
*Root color.*—White (RHS 155C) to cream white, getting brown if too wet.

Stems:
*Number of stems per plant.*—4 main shoots with side shoots.
*Length.*—About 10.0 cm.
*Diameter.*—0.4 cm.
*Internode length.*—1.3 cm.
*Color.*—RHS 138B.
*Texture.*—Pubescence.
*Anthocyanin.*—Absent.

Leaves:
*Arrangement.*—Single, opposite.
*Type.*—Simple.
*Shape.*—Ovate.
*Number of leaves per branch.*—5 pairs, without side shoots and their leaves.
*Variegation.*—Absent.
*Apex.*—Acuminate.
*Base.*—Cordate.
*Margin.*—Serrate.
*Length.*—Between 1.0 cm to 3.0 cm.
*Width.*—Between 0.9 cm and 2.7 cm.
*Color.*—Immature leaf: Upper surface: RHS 139A. Lower surface: RHS 139C. Mature leaf: Upper surface: RHS 139A. Lower surface: RHS 139C.
*Texture.*—Both upper and lower surfaces: Leathery.
*Venation type.*—Pinnate.
*Venation color.*—Upper surface: RHS 139A. Lower surface: RHS 139C.
*Petiole.*—Length: Immature leaf: 0.05 cm. Mature leaf: 0.3 cm. Diameter: 0.2 cm. Texture: Pubescence. Color: RHS 138B.

Inflorescence:
*Blooming habit.*—Freely flowering.
*Quantity of inflorescence per stem.*—7.
*Type of inflorescence.*—Single, salverform.
*Persistent or self-cleaning flower.*—Self-cleaning flower.
*Fragrance.*—Present but only foliage not flowers.

Peduncle:
*Length.*—0.6 cm.
*Diameter.*—0.1 cm.
*Color.*—RHS 138A.
*Texture.*—Pubescence.
*Strength.*—Thin.

Bud:
*Shape.*—Tubular.
*Diameter.*—0.5 cm.
*Length.*—0.7 cm.
*Color* (*at tight bud*).—RHS 138D.

Corolla (flower):
*Type and shape.*—Single-type, nearly round, lower part tube and funnel.
*Corolla, horizontal diameter.*—2.6 cm.
*Corolla, total length.*—1.1 cm.
*Color of throat.*—Inner surface: RHS 23A. Outer surface: RHS 18A.
*Tube/funnel.*—Length: 0.6 cm. Diameter: 0.5 cm. Texture of funnel: Inner surface: Leathery. Outer surface: Leathery.

Petal (lobes):
*Length.*—1.2 cm.
*Width.*—1.0 cm.
*Apex.*—Rounded tips.
*Base.*—Fused to a tube.
*Margin.*—Entire.
*Color.*—Inner surface: RHS 157D. Outer surface: RHS 157D.
*Texture.*—Upper surface: Leathery. Lower surface: Leathery.

Calyx:
*Arrangement and appearance.*—Whorl of 5 sepals surrounding the base of the flower tube, sepals are fused at the base.
*Sepals.*—Color: Upper surface: RHS 138A. Lower surface: RHS 138A. Length: 0.7 cm. Width: 0.2 cm. Shape: 5 sepals fused at the base. Apex: Acuminate. Base: Fused. Margin: Entire. Texture: Upper surface: Pubescence. Lower surface: Pubescence.

Reproductive organs:
*Stamens.*—Quantity: 4. Filament: Color: RHS 138D. Length: 1.2 cm. Diameter: 0.2 cm. Anther color: RHS 13A. Pollen amount: Abundant. Pollen color: RHS 13A.
*Pistil.*—Quantity per flower: 1. Length: 1.1 cm. Stigma color: RHS 139C. Style color: RHS 139C. Style length: 1.0 cm. Ovary color: RHS 139C.

Fruit and seed set: Fruit and seed is observed.
Disease and pest/insect resistance: None observed.

COMPARISON WITH PARENTAL LINES AND KNOWN VARIETY

'KLESG22036' is a distinct variety of *Sutera* having a white flower color; 'KLESG22036' is distinguished from its parents as described in Table 1:

TABLE 1

Comparison with Parental Lines

| Trait | Variety 'KLESG22036' | Female parent Scopia ® Compact White (patent status unknown) | Male parent 'SG-2016-0688' (unpatented) |
|---|---|---|---|
| Internode length | Short | Long | Short |
| Flower size | Large | Medium | Medium |

'KLESG22036' is most similar to the *Sutera* plant named 'KLESG13255' (U.S. Plant Pat. No. 26,080). Differences between the two varieties are described in Table 2:

TABLE 2

Comparison with Similar Variety

| Trait | Variety 'KLESG22036' | Similar variety 'KLESG13255' |
|---|---|---|
| Flower size | Big flower | Medium flower |
| Internode length | Short (compact growth) | Long (stretching needs PGR) |
| Summer performance | Good | Often flower breaks, low performance |

I claim:

1. A new and distinct cultivar of *Sutera* Plant Named 'KLESG22036' as described and illustrated herein.

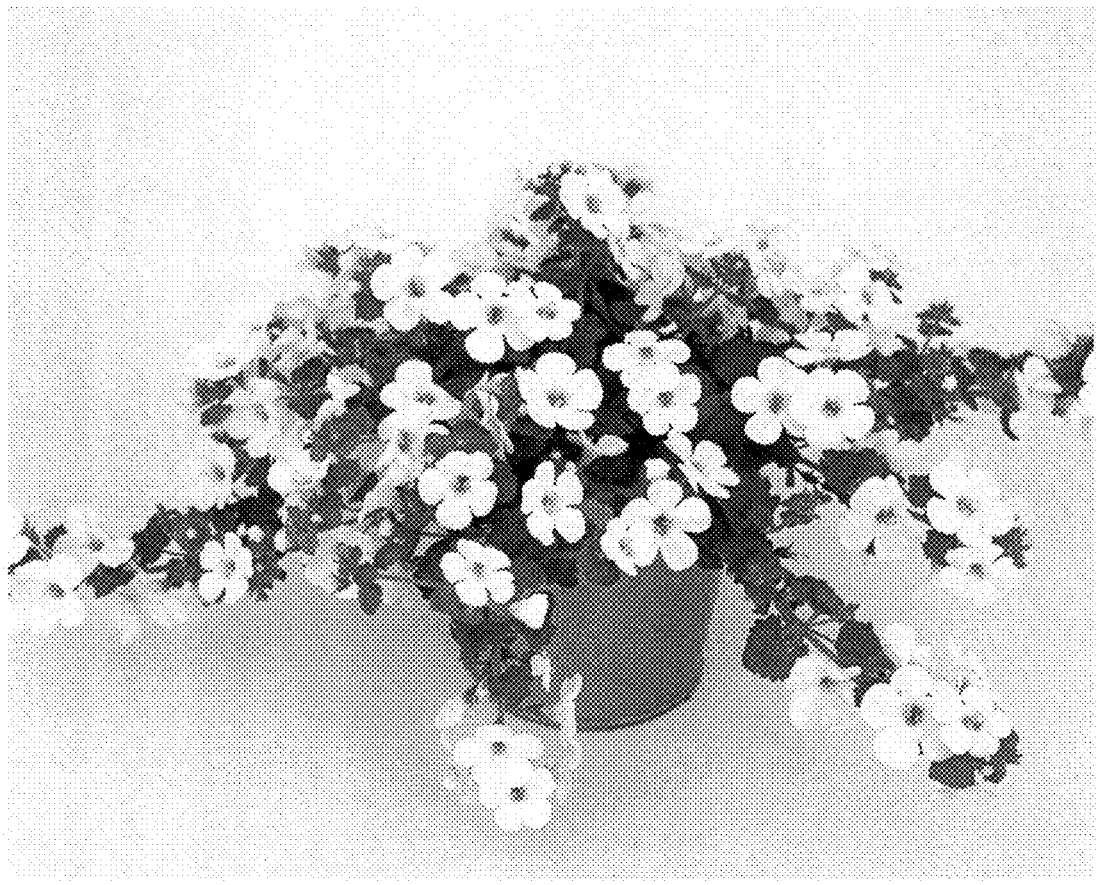

* * * * *